351-243 SR
6/2/87 OR H 000,293

United States Statutory Invention Registration [19]

[11] Reg. Number: H293

Task et al. [43] Published: Jun. 2, 1987

[54] PORTABLE VISUAL FUNCTION TESTER

[75] Inventors: Harry L. Task, Dayton; Louis V. Genco, Enon, both of Ohio

[73] Assignee: The United States of America as represented by the Secretary of the Air Force, Washington, D.C.

[21] Appl. No.: 869,150

[22] Filed: May 29, 1986

Related U.S. Application Data

[63] Continuation of Ser. No. 599,088, Apr. 11, 1984, abandoned.

[51] Int. Cl.[4] ..... A61B 3/02

[52] U.S. Cl. ..... 351/243; 351/222; 351/240

[58] Field of Search ..... 351/222, 237, 239, 240, 351/241, 242, 243

[56] References Cited

U.S. PATENT DOCUMENTS

| | | | |
|---|---|---|---|
| 2,326,965 | 8/1943 | Neumueller | 351/239 |
| 3,532,418 | 5/1968 | Schainholz et al. | 351/36 |
| 3,535,026 | 10/1970 | Coss | 351/1 |
| 3,737,217 | 6/1973 | Haines et al. | 351/23 |
| 3,891,311 | 6/1975 | Fletcher et al. | 351/38 |
| 3,936,163 | 2/1976 | Toth | 351/17 |
| 4,027,954 | 6/1977 | Good | 351/36 |
| 4,368,959 | 1/1983 | D'Amato | 351/243 |

*Primary Examiner*—Stephen C. Buczinski
*Assistant Examiner*—Linda J. Wallace
*Attorney, Agent, or Firm*—Donald J. Singer; Bobby D. Scearce; Thomas L. Kundert

[57] ABSTRACT

A portable visual function tester and testing method is described for rapid and accurate measurement of several human vision parameters, including critical fusion frequency, stereopsis, Snellen visual acuity and visual resolution, cyclophoria, eye dominance, and lateral and vertical phoria, which comprises, first and second illuminated visual displays disposed for viewing by respective left and right eyes of a subject along respective parallel first and second optical axes, each display comprising an array of visual display patterns, one pattern of each display comprising a pair disposed for simultaneous viewing by the subject in the measurement of a corresponding vision parameter; the display patterns include an illuminated blinking disk for measurement of critical fusion frequency, a rectangular array of four-dot sets for measurement of stereopsis, an array of Snellen E designs of various sizes and orientations for measurement of visual acuity, and a resolution fan comprising a pattern of a plurality of radially extending alternate bright and dark luminance areas for measurement of minimum visual resolution; the visual display pairs include a first pair including a first circle with adjacent reference mark and a second circle with adjacent reference scale for measurement of cyclophoria, a second pair including two sets of oppositely oriented diagonal lines for determination of eye dominance, and a third pair including an illuminated dot and illuminated rectangular grid for testing of lateral and vertical phorias; suitable electronics are included for selectively illuminating the display patterns in pairs.

22 Claims, 13 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

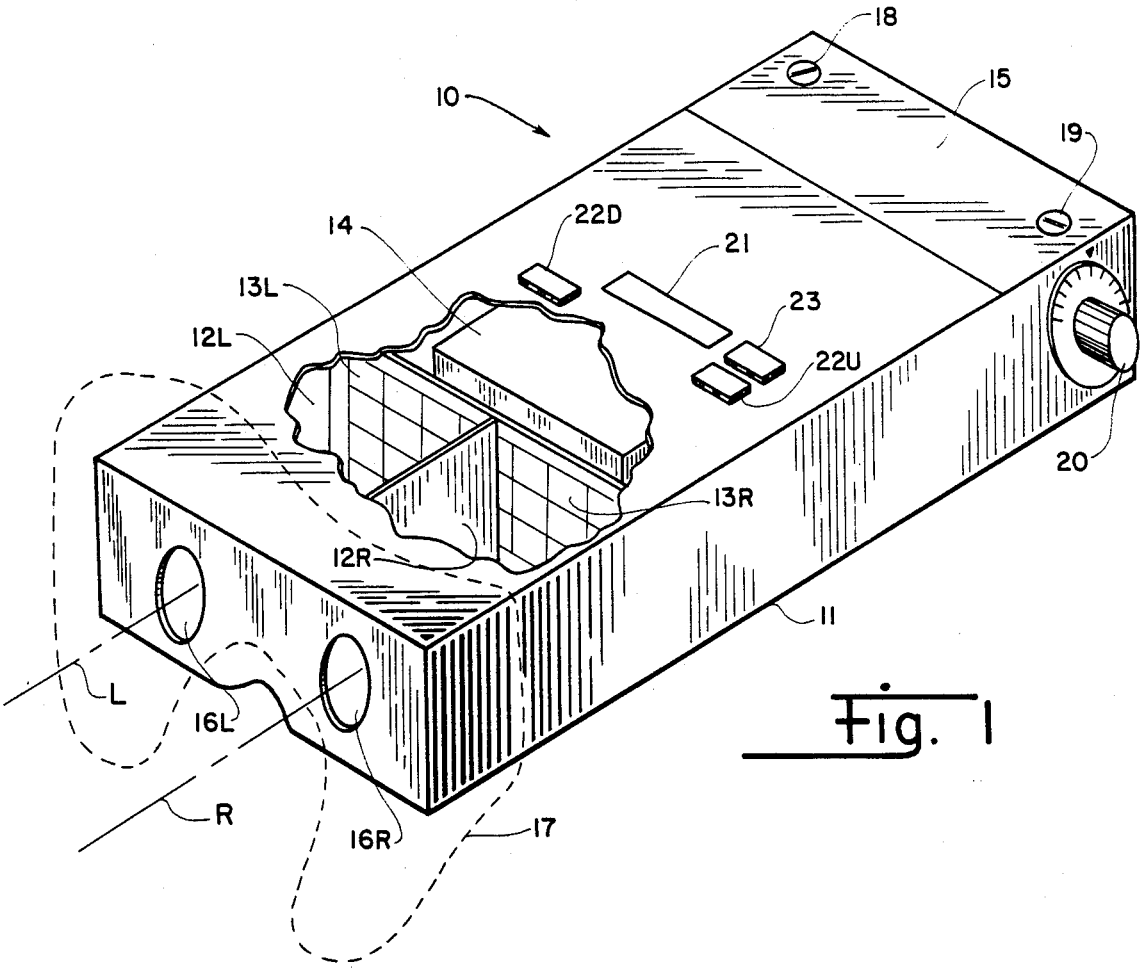
Fig. 1
Fig. 5
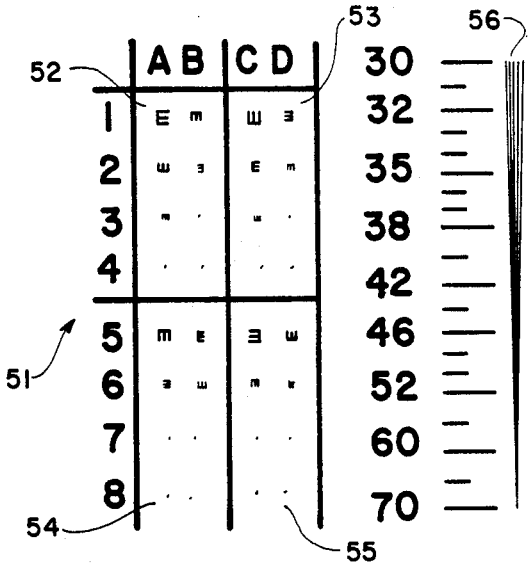

PORTABLE VISUAL FUNCTION TESTER

RIGHTS OF THE GOVERNMENT

The invention described herein may be manufactured and used by or for the Government of the United States for all governmental purposes without the payment of any royalty.

This is a continuation of application Ser. No. 06/599,088, filed Apr. 11, 1984, now abandoned.

BACKGROUND OF THE INVENTION

The present invention relates generally to vision testers and vision testing methods, and more particularly to a novel system and method for testing a plurality of human vision parameters.

Many astronauts have commented on apparent vision problems during earth orbit, including supposed "supervision" by pre-Gemini astronauts, and, more recently, complaints including reduction in near visual acuity with no apparent change in distant vision, significant elevation of intraocular pressure, "misplaced horizon", and increased dependence upon reading glasses. Although the literature contains numerous reference to various anticipated effects of orbital environmental conditions upon human vision, few actual tests were performed since suitable instrumentation and testing methods have not heretofore existed for use in quantifying changes in all the numerous human vision parameters of interest under orbital conditions. The prior tests which were conducted included out-the-window visual acuity measurements using sightings of ground targets from Gemini V and VII, and a near-vision test series on accommodative amplitude performed on STS-5 and later flights.

The present invention comprises a compact, portable, and battery powered system and vision testing method for the rapid measurement of a plurality of human vision parameters, including critical fusion frequency, stereopsis. Snellen visual acuity and visual resolution, cyclophoria (torsional phoria), eye dominance (retinal rivalry), and lateral and vertical phoria. The visual function tester of the present invention combines a dual optical system with a broad spectrum of illuminated visual test patterns in a compact, portable unit which may find particular utility for the definition and measurement of the environmental and physiological effects on a broad range of human vision parameters, such as changes in these parameters under the effects of orbital space flight.

The system of the present invention is self powered and uses microelectronic circuitry controlled light emitting diode (LED) displays to create a series of controlled illumination stimulus patterns at or near optical infinity, for use in measuring a plurality of visual functions, with a separate stimulus pattern or set of patterns configured for testing each such visual function. The unique arrangement of all test patterns within the same field of view allows each pattern to be used by electronically switching the appropriate LED, thus eliminating the need for any mechanical moving parts with the exception of the switch. This improves the optical alignment and ruggedness of the system as there are no moving parts to wear or become misaligned. Data may be recorded verbally by the subject on a microcassette audio recorder which may be included as a part of the electronics of this system; the subject may indicate verbally the test number and observed results as shown in the vision function tester.

It is, therefore, a principal object of the present invention to provide a novel portable visual function tester and method for measuring a plurality of human vision parameters, including critical fusion frequency, stereopsis. Snellen visual acuity and visual resolution, cyclophoria (torsional phoria), eye dominance (retinal rivalry), and lateral and vertical phoria.

It is a further object of the present invention to provide a visual function tester for measuring the environmental effects on the various named human vision parameters.

It is a further object of the invention to provide a system and method for quantifying changes in certain human vision parameters under the effects of orbital space flight.

It is still another object of the invention to provide a method for testing the effects of various environmental conditions on the named human vision parameters.

These and other objects of the present invention will become apparent as the detailed description of certain representative embodiments thereof proceeds.

SUMMARY OF THE INVENTION

In accordance with the foregoing principles and objects of the present invention, a novel portable visual function tester and reliable testing method is described for the rapid and accurate measurement of several parameters of human vision, including critical fusion frequency, stereopsis. Snellen visual acuity and visual resolution, cyclophoria (torsional phoria), eye dominance (retinal rivalry), and lateral and vertical phoria, which comprises, first and second illuminated iosual displays disposed for viewing by the respective left and right eyes of the subject along respective parallel first and second optical axes, each of the displays comprising an array of visual display patterns, one pattern of each of the first and second displays comprising a pair disposed for simultaneous viewing by said subject in a particular vision test in the measurement of a corresponding vision parameter; the visual display patterns include an illuminated blinking disk for use in measurement of critical fusion frequency, a rectangular array of four-dot sets for measurement of stereopsis, an array of Snellen E designs of various sizes and orientations for the measurement of visual acuity, and a resolution fan comprising a pattern of a plurality of radially extending alternate bright and dark luminance areas for the measurement of minimum visual resolution; the visual display pairs may include a first pair including a first circle with reference mark adjacent thereto and a second circle and a reference scale adjacent thereto for the measurement of cyclophoria, a second pair including two sets of oppositely oriented diagonal lines for the determination of eye dominance, and a third pair including an illuminated dot and an illuminated rectangular grid pattern for testing of lateral and vertical phorias; suitable electronics are included for selectively controlling the illumination of the display patterns in pairs. The visual display patterns may comprise light emitting diodes. The electronics of the system may further include an audio recorder for recording the identifications of the selected vision parameter measurement and the results of observations using the system, and may be battery powered for portability.

DESCRIPTION OF THE DRAWINGS

The present invention will be more clearly undestood from the following detailed description of certain representative embodiments thereof read in conjunction with the accompanying drawings wherein:

FIG. 1 is a perspective view of a representative visual function tester of the present invention with part of the housing broken away to reveal certain of the internal components thereof.

FIG. 5 is a schematic on enlarged scale of the representative test pattern included in the FIGS. 2 and 3 displays which may be used for high contrast (high resolution) Snellen and minimum resolution acuity tests.

DETAILED DESCRIPTION

Figure 2:
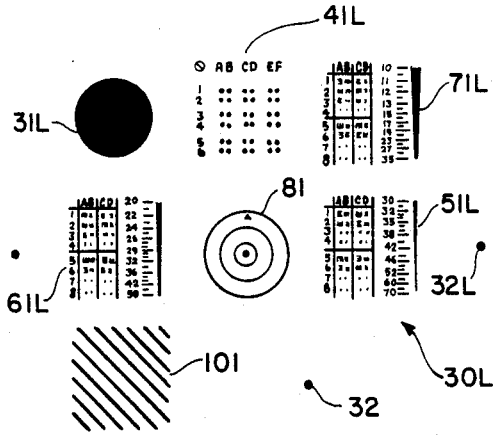
FIG. 2 is a schematic of a set of representative visual test display patterns, on substantially enlarged scale, for illumination and display to one eye in the testing of the various human vision parameters described herein.

Referring now to the drawings, FIG. 1 presents a perspective view of a representative embodiment of the visual function tester (VFT) 10 of the present invention. Part of the housing for the tester depicted in FIG. 1 is shown broken away in order to reveal certain of the internal components of the tester.

The tester 10 of the present invention may preferably comprise a housing 11 including three sections for enclosing a pair of viewing sections 12L and 12R containing, respectively, visual test displays 13L,13R for vision testing as hereinafter described. The middle section of tester 10 may include the electronics 14 including the logic, display, information processing, and control functions for the visual displays 13L,13R, and audio recording means for information recording. Battery compartment 15 may comprise the power source for operation of tester 10. Housing 11 may further comprise a pair of eyepiece lenses 16L,16R through which a subject may view the visual display 13L,13R in the performance of visual tests using tester 10. Lenses 16L,16R act as simple magnifiers to create virtual images of the displays 13L,13R. The images are presented along respective parallel optical axis L,R for each respective eye of the subject. A padded forehead rest/hood 17 (shown in phantom) may be included if desired to provide a forehead cushion and shield against extraneous light for the subject during vision tests. On/off switch 18, momentary push button control/function interrupter 19, and multiple postion function test selector switch 20, all operatively interconnected with the electronics 14 and power source 15 may be located in conveniently accessible positions such as suggested in FIG. 1. Frequency readout display 21, frequency increase control button 22U, frequency decrease control button 22D, and frequency reset button 23, also operatively interconnected with and forming a part of electronics 14 may be located on housing 11 as shown. In a non-limiting, representative tester 10 built in demonstration of the invention herein, the overall size of housing 11 was about 5"×12"×2".

Displays 13L,13R, described in more detail below in relation to FIGS. 2 through 12, contain the various visual displays for testing the various vision parameters utilizing tester 10. Each display 13L,13R includes an array of display patterns in the form of light emitting diodes (LED's), each display pattern being individually controllable as hereinafter described. In the tester 10 demonstration unit the LED's (except as othewise specifically indicated) were selected as green on color for optimum visibility.

In the performance of visual tests utilizing tester 10, the user/subject looks through lenses 16L,16R and rotates swtich 20 to the appropriate setting for the desired visual test. Data may be recorded verbally on a microcassette audio tape recorder included in electronics 14 and mounted under the device; the subject reads the test number and the results as shown through viewing of the various display patterns.

Described below individually are the battery of tests included in the tester 10 built in demonstration of the invention. The selection of tests was made on a basis of detecting changes in critical vision parameters resulting from neurological or muscular balance changes caused by weightlessness.

Figure 3:
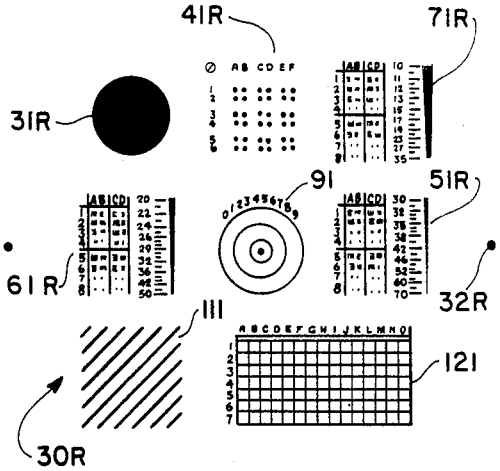
FIG. 3 is a schematic of a set of representative visual test display patterns, corresponding to respective patterns of FIG. 2, for illumination and display to the other eye in the testing of the various human vision parameters described herein.

Referring now to FIGS. 2 and 3, the patterns comprising visual test displays 13L,13R of FIG. 1 are presented in more detail, respectively, as pattern arrays 30L,30R. Each pattern in the arrays 30L,30R may be individually controllable and may preferably comprise an LED display, the patterns being controllable in pairs for each named vision test to expose a pattern of 30L to the left eye and a companion pattern of 30R to the right eye. It is understood that the selection of displays presented to the left and right eyes, respectively, in the use of tester 10 may, within the teachings hereof, be reversed for any of the visual tests performed. In the tester 10 unit built in demonstration of the invention herein, patterns 31L,31R comprised substantially identical controllable blinking circular light discs for the measurement of critical fusion frequency; substantially identical patterns 41L,41R were configured for testing of stereopsis; patterns 51L,51R and 61L,61R and 71L,71R were configured for visual acuity and resolution tests; patterns 81,91 were configured to test for cyclophoria; patterns 101,111 were configured to test for eye dominance; and patterns 32, 121 were configured to measure lateral and vertical phoria.

Patterns 31L,31R each comprise a circular light which may be made to blink at a controllable frequency, for use in the testing of critical fusion frequency. In the functioning of the body's nervous system, data is transmitted between our sensory organs, brain and muscles via frequency-encoded nervous transmissions. Whenever a nerve fires, it must "rest" a while before firing again, which resting, or latency period varies depending on many factors, including physiological state. One way to measure the nerves' ability to conduct signals is to input a known signal varying in frequency over time at a sense organ, and test the brain's ability to detect the signal. A simple example is critical fusion frequency (CFF) or flicker fusion frequency (FFF). A blinking light is presented to the eyes, and the blink frequency is increased until the light fuses or appears steady and unblinking. This critical fushion frequency is an indication of the physiological state of the nervous system. If CFF changes, nervous transmission speed may have been affected due to fatigue or other physiological change occuring at the synapses, thus affecting our ability to properly gather and analyze sensory data. Normal CFF may be between 50 Hz and 70 Hz, depending on several factors, including the portion of the retina which is stimulated. Patterns 31L,31R each comprised a circular pattern (approximately 5° in diameter) retro illuminated by a yellow-green flat LED. The LED was configured to emit square wave blinks and to be frequency controlled by the electronics 14.

In the performance of a CFF test, the subject presses the DOWN (left) button 22D until the steady light is just seen to flicker. He then looks out of the instrument at the seven-segment LED frequency display 21 on top of housing 11 and presses the frequency button 23 and verbally records the reading. The subject then looks into the device and presses the UP (right) button 22U until the flickering light is seen as steady, and agains looks outside the device at the frequency display 21, and presses the frequency button 23. The number indicated on the display is the CFF in Hertz. The subject verbally records this value, then presses the DOWN button to lower the frequency past his threshold for a repeat test. This test (foveal flicker fusion frequency) is repeated several times, after which the subject looks at a fixation doe 32L,R located several degrees to the right of the CFF disc 31, and repeats the test several more times. This later test measures the peripheral flicker fusion frequency.

Figure 4L:
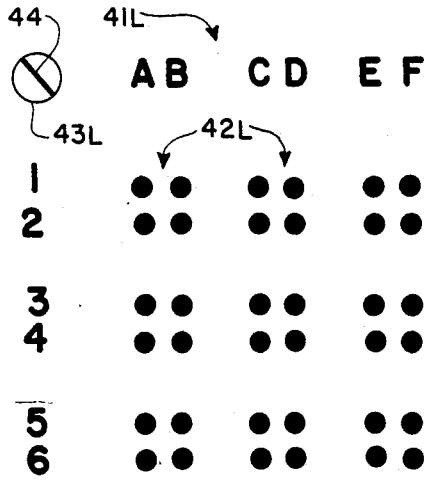
FIG. 4L is a schematic on enlarged scale of the representative test pattern included in FIG. 2 which may be presented to the left eye for measurement of stereopsis.
Figure 4R:
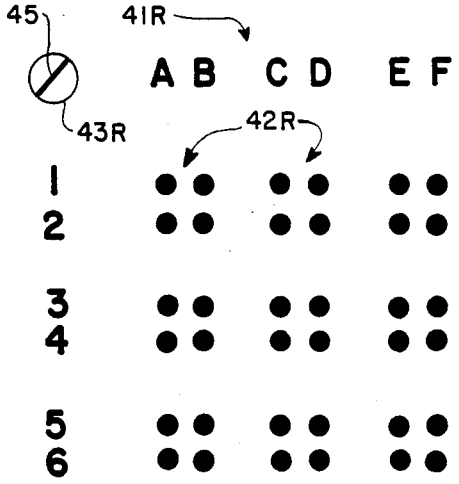
FIG. 4R is a schematic on enlarged scale of the representative test pattern included in FIG. 3 which may be presented to the right eye for measurement of stereopsis.

Referring now to FIGS. 4L and 4R, presented therein are enlarged views of the respective patterns 41L,41R shown in the display pattern arrays 30L,30R of FIGS. 2 and 3, respectively, for testing of stereopsis (clinical depth perception) and suppression. Although there are at least six visual cues to depth perception, many of them are absent in the textureless visual environment encountered when looking outside a spacercraft. Stereopsis (a function of retinal disparity) may then be of increased importance to the safety and control of docking, untethered maneuvers and other nearby operations and may be tested to detect decrement in this parameter due to capsule environmental conditions or physiological changes in the crew. Stereopsis requires fine fusional control and a high level of cerebral interpretation of visual data. Under laboratory conditions, some people have displayed stereoacuity as fine as two seconds of arc. These individuals are able to see a difference in depth between similar objects placed at "infinity" and at 6550 meters.

In the test of stereopsis, a rectangular array of a plurality of four-dot sets 42L,42R are presented to the subject. The subject identifies (by column and row identifiers) which display pattern 42 is observed, and which dot on each set appears to be closer than the others.

One reason for degraded stereopsis is suppression, or the selective "turning off" of all a portion of the field of view of one eye. The upper left corner of the stereopsis test slide contains a macular suppression test. The test consists of a pair of identically sized circles 43L,43R (seen by both eyes) with a diagonal line 44 ( ) through circle 43L as viewed by the left eye, and diagonal line 45(/) through circle 43R as viewed by the right eye. If the subject sees only one diagonal line (44 or 45), he is suppressing one eye; if he sees an "X" both eyes are working together.

FIG. 5 presents an enlarged view of the (identical) patterns 51L,51R for the high contrast, high resolution Snellen acuity test to determine what is the smallest letter the subject can read, and how far away the subject can read letters.

The left part of the acuity test patterns 51 contains four rectangles 52-55, identified by coordinates numbered from 1 through 8, and lettered from A through D, each containing a plurality of Snellen "E" designs of various sizes and orientations. In the conduct of a test, the subject indicates the orientation of each Snellen "E" with each rectangle. This test indicates the smallest (most distant) resolvable letter or multiple spatial frequency.

Patterns 51L,R may also be used in the determination of minimum resolution acuity, i.e. what is the smallest separation or dtail which one can see. Accordingly, the right part of the pattern contains a spatial resolution (RETMA) fan 56 and an accompanying series of identifying numbers and pointer lines. The subject indicates the number corresponding to the level (spatial frequency) at which the distinct fan 56 lines appear to blur or merge. The corresponding number represents the spatial frequency of the fan in cycles per degree, at the point indicated.

Figure 6:
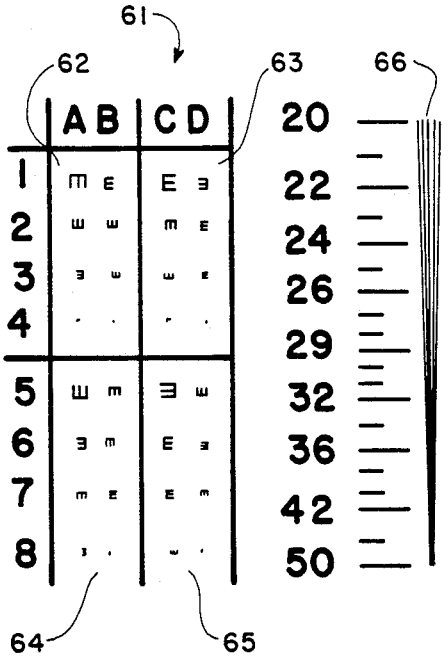
FIG. 6 is a schematic on enlarged scale of the representative test pattern included in the FIGS. 2 and 3 displays which may be used for performing a medium illumination mesopic visual acuity test if fitted with an appropriate neutral density filters.
Figure 7:
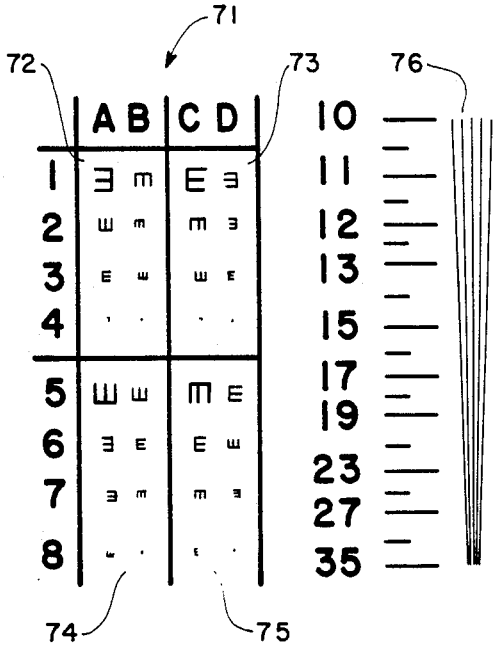
FIG. 7 is a schematic on enlarged scale of the representative test pattern included in the FIGS. 2 and 3 displays which may be used for performing a low illumination mesopic visual acuity test if fitted with somewhat denser neutral filters.

FIG. 6 presents an enlarged view of the (identical) patterns 61L,R, similar in arrangement and function to pattern 51L,R of FIG. 5. Each pattern 61L,R contains rectangles 62-65 including Snellen "E" designs and a resolution fan 66 of frequency range different from that of fan 56. Patterns 61L,R are designed for a medium illumination mesopic visual acuity test, i.e., how well one can see in dim light. FIG. 7 presents an enlarged view of (identical) patterns 71L,R including rectangles 72-75 and Snellen "E" designs of various sizes and orientations, and a resolution fan 76 for a low illumination mesopic visual acuity test. Because of the absence of atmosphere and other light-scattering particulates in space, objects seen against the starry background will always be of high contrast. The addition of tinted visors and other transparent materials reduces the transmitted light energy, but may not affect contrast (unless dirty or of poor quality). Lowering the overall light level impingent on the retina will cause the visual system to shift from photopic through mesopic to scotopic vision. The effect of the visual environment found in space on mesopic and scotopic visual performances may therefore be studied. Patterns 61L,R and 71L,R may further be used in conjunction with appropriate neutral density filters to provide luminances in the mesopic ranges, in addition to providing alternative illumination visual acuity tests in the photopic range.

Normally, tilting one's head to the right or left will result in the eyes torquing slightly in the opposite direction to attempt to compensate, and to keep the retinal image of the horizon horizontal. There is evidence indicating head tilt (as detected by the semicircular canals of the ear) is partially compensated in our visual system by activity of the oblique muscles of the eyes. This linkage may contribute to a better perception of ones position in space with respect to the horizon. In space, gravity does not provide cues for "true" vertical, and the semicircular canals are relatively useless. In addition, the otolith mechanism is rendered ineffectual by a combination of weightlessness and decalcification of the tiny otoliths themselves. Interference with these linkages appears to contribute to symptoms of vertigo.

Figure 8:
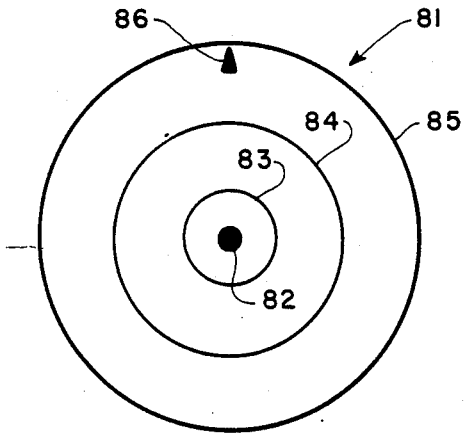
FIG. 8 is a schematic on enlarged scale of the representative test pattern included in the FIG. 2 display which may be used for exposure of the left eye in the testing for cyclophoria (torsional phoria).
Figure 9:
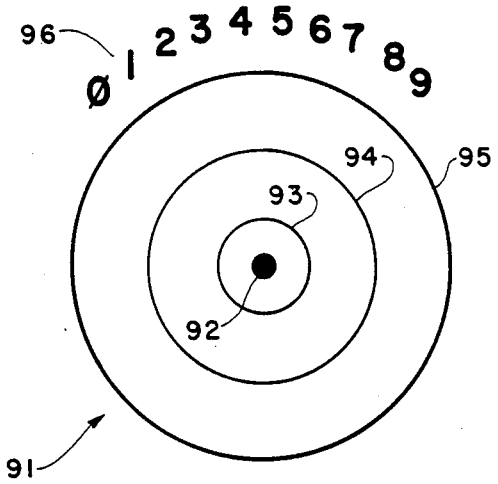
FIG. 9 is a schematic on enlarged scale of the representative test pattern included in the FIG. 3 display which may be used in conjunction with the pattern of FIG. 8 and for exposure to the right eye in the testing for cyclophoria (torsional phoria).

FIG. 8 is an enlarged view of pattern 81 of display 30L for exposure to one eye of the subject (e.g., the left eye) in a cyclophoria (torsional phoria) test. FIG. 9 is an enlarged view of pattern 91 of display 30R for exposure to the other eye (i.e. the right eye in the demonstration tester 10 constructed) for a cyclophoria test. This test is designed to determine the relative positions of the eyes along a vertical axis. Each pattern 81,91 comprises a central dot 82,92 and a plurality of concentric circles 83–85 and 93–95. When viewed simultaneously, the circles serve to fuse the patterns for vertical and horizontal displacements, while allowing free torsional movements. There is no fusion stimulus for torsion. Accordingly, pattern 81 includes a reference mark or arrow 86 which is viewed as adjacent a reference scale 96 on pattern 91 when the two patterns 81,91 are viewed simultaneously. The subject identifies at which number on scale 96 the arrow 86 points, each numbered index mark on scale 96 representing ten degrees of rotation. If the eyes have not rotated, the subject will report the arrow 86 pointing to 4.5 on scale 96.

Figure 10:
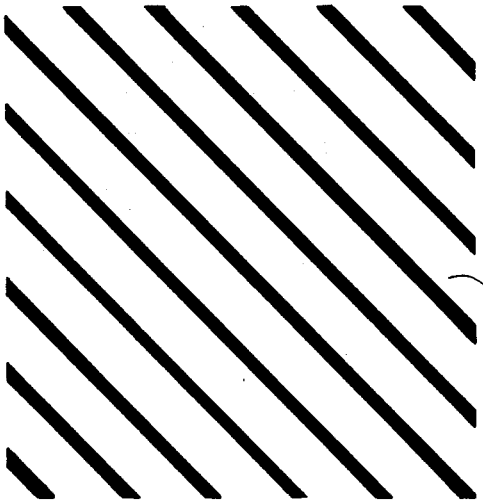
FIG. 10 is a schematic on enlarged scale of the representative test pattern included in the FIG. 2 display which may be used for exposure to the left eye in testing for retinal rivalry.
Figure 11:
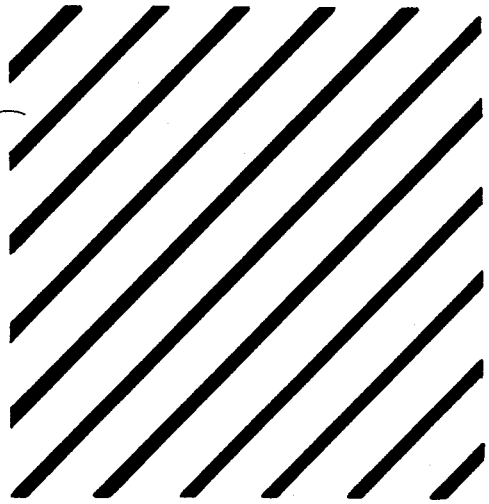
FIG. 11 is a schematic on enlarged scale of the representative test pattern included in the FIG. 3 display which may be used in conjunction with the pattern of FIG. 10 and for exposure to the right eye in the testing for retinal rivalry.
Figure 12:
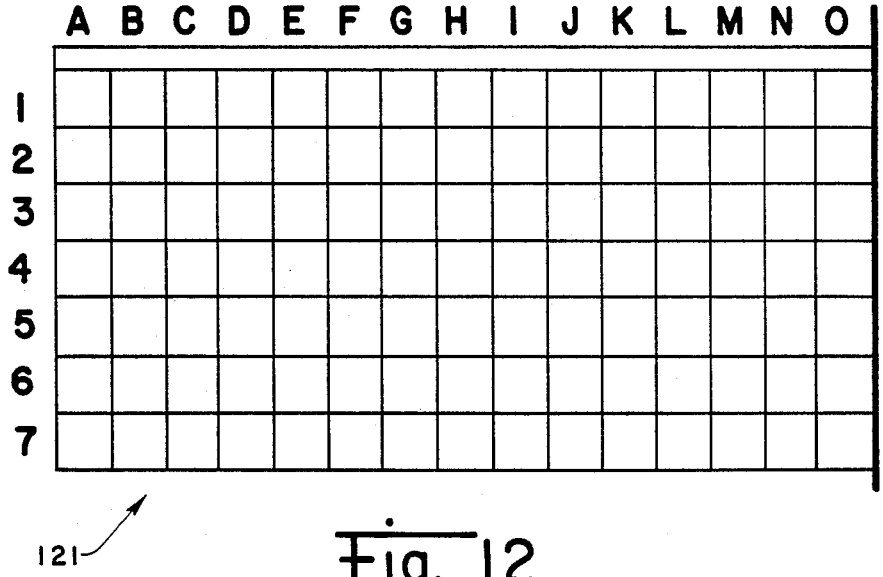
FIG. 12 is a schematic on enlarged scale of a test grid pattern included in the FIG. 3 display which may be presented to one eye and used in conjunction with a momentarily flashed dot presented to the other eye in testing for lateral and vertical phorias.

FIGS. 10 and 11 present enlarged views of patterns 101 and 111 of display 30L and 30R, respectively, of FIGS. 2 and 3. These patterns are designed to measure retinal rivalry, i.e., if one eye or one cerebral hemisphere is more dominant than the other. In the nonlimiting examples given, the pattern 101 of FIG. 10 comprised a green-colored diagonal LED pattern display, for viewing by one eye (e.g., the left eye in the example given), and pattern 111 of FIG. 11 comprised a red-colored oppositely oriented diagonal LED pattern display, for viewing by the other eye.

The use of heads-up displays (HUD) and helmet-mounted displays (HMD) in aircraft has underlined the importance of binocular vision. If single simultaneously binocular vision is degraded by weightlessness or other conditions, certain haploptically presented visual displays will also be effected. If imagery is presented only to one eye, and different visual information to the other, retinal rivalry will cause only portions of each image to be "seen" at any one time. Typically, the perceived scene shifts back and forth, depending which eye (or field of view) is "dominant" for that moment. One way to test retinal rivalry is to measure the rate at which the eyes trade dominancy, and the duration for which each eye is dominant.

Normally, the lines of sight (imaginary lines extending from the fovea of each eye) intersect at the object of regard. When a subject is extremely stressed or fatigued, or under the influence of drugs or alcohol, or otherwise dissociated, the lines of sight of each of his eyes move toward a "position of rest." For most subjects, this latter position is dissimilar from that assumed by the eyes when in a normally alert state. If a subject's lines of sight no longer intersect the point of regard when his eye's vision is dissociated from the other, that subject is said to have a "heterophoria". In subjects with high heterophorias, the visual system has to work harder to prevent double vision. On Earth, heterophorias usually remain fairly constant over short (day to day) periods. Little information is available on the favored position of the eyes while in space.

The novel patterns of tester 10 useful for measuring the magnitude and direction of lateral and vertical heterophoria are shown as dot 32 in FIG. 2, and grid pattern 121 of FIG. 3. Pattern 121 is shown in enlarged scale in FIG. 12.

Some individuals' lines of sight are such that both eyes are not aligned with the object of regard. These individuals are said to have heterotropias. Tester 10 may be used to detect and measure the magnitude and direction of both vertical and horizontal (lateral) heterotropias or heterophorias. In the nonlimiting test pattern example given, the stimulus for the left eye comprises flashing dot 32 which is initially invisible at the start of the test. When flashing dot 32 is actuated, one eye (e.g., the left eye for the tester 10 constructed) sees a short-duration flash. In tester 10, frequency button 23 acted as the stimulus button for the flashing dot 32 for the test selector 20 position corresponding to the tests for lateral and vertical phorias. The stimulus for the other (right) eye consists of an LED display of lettered and numbered matrix or grid 121 of squares of FIG. 12. When the stimulus button is pressed, a single dot of light appears only to the eye that does not see the grid pattern. The subject identifies in which square the bright dot 32 is located when the dot 32 and grid 121 are viewed simultaneously. The brain fuses these two images (the grid and the dot) into one. By knowing the optical and mechanical alignment of the device it is possible to determine the amount of lateral and vertical muscle imbalance (phoria) between the eyes. If these is no imbalance, the dot will appear in the center of the grid 121 (4—H in the representative tester 10). Each square to the left of this position corresponds to 10 milliradians or one prism diopter of esophoria (eyes tend to be cross-eyed) and each square to the right corresponds to one prism diopter of exophoria. Vertical displacements of the dot correspond to one prism diopter of vertical phoria per grid 121 square. Using this technique it is possible to achieve a measurement accuracy of about ½ prism diopter. If the flash of dot 32 occurs too fast to note the position of the dot, the subject can press the frequency button 23 to repeat the test.

The tester 10 demonstration unit was used to perform the names tests on a select group of individuals to determine the utility of the device to provide reliable test results, both as to repeatability of group data and to reproducibility of individual baseline values of each test. Results of the demonstration tests indicated an extremely close compatibility of the data, assuring that differences in measurements were due to changes in the visual function being measured rather than in the instrument.

The present invention, as hereinbefore described, therefore provides a novel portable system of excellent sensitivity, and a highly reliable vision testing method for the measurement of several characteristics of human vision, including critical fusion frequency, stereopsis, Snellen visual acuity and visual resolution, cyclophoria (torsional phoria), eye dominance (retinal rivalry), and lateral and vertical phoria. It is understood that certain modifications to the invention may be made, as might occur to one with skill in the field of this invention, within the scope of the appended claims. For example, a variation of the invention may include means whereby either the lens plane or the pattern display plane could move so that the distance of the virtual image could be changed to allow the mesurement of the above parameters at different eye accommodations states. Therefore, all embodiments contemplated hereunder which achieve the objects of the present invention have not been shown in complete detail. Other embodiments may be developed without departing from the spirit of the invention or from the scope of the appended claims.

We claim:

1. A vision testing system for measuring a plurality of vision function parameters of a subject, which comprises:

a. first and second illuminated visual displays disposed for viewing along respective parallel first and second optical axes, said first display disposed for viewing by a first eye only of said subject along said first axis, and said second display disposed for viewing by the second eye only of said subject along said second axis;

b. each of said first and second displays comprising an array of a plurality of visual display patterns, one pattern of said first display and a corresponding pattern of said second display comprising a pair for simultaneous viewing by said subject, said first and second displays including a pair having dissimilar patterns, each pair being utilized in a particular vision test in the measurement of a corresponding vision function parameter;

c. means for selectively controlling the illumination ~~of~~ each pair of said display patterns for viewing by said subject of any preselected pair in measurement of the corresponding vision function parameter; and d. optical means including first and second eyepiece lenses disposed, respectively, along said first and second optical axes through which said first and second displays are viewed by respective first and second eyes of said subject, said eyepiece lenses configured to project images of each of said first and second displays to optical infinity.

2. The system as recited in claim 1 wherein said visual display patterns comprise light emitting diodes.

3. The system as defined in claim 1 further comprising recording means for verbally recording the identification of the preselected vision parameter measurement and the results of observations with respect to the said measurement.

4. The system as recited in claim 1 wherein said visual display patterns include an illuminated disk, and said system further comprises means for selectively illuminating said disk at a controllable frequency, and means for selectively varying that frequency, for the measurement of critical fusion frequency of the eyes of said subject.

5. The system as recited in claim 1 wherein said visual display patterns include a rectangular array of patterns comprising four-dot sets for the measurement of stereopsis in said subject.

6. The system as recited in claim 1 wherein said visual display patterns include an array of Snellen E designs of various sizes and orientations for the measurement of visual acuity of said subject.

7. The system as recited in claim 1 wherein said visual display patterns include a resolution fan comprising a pattern of a plurality of radially extending alternate bright and dark luminance areas for the measurement of minimum visual resolution of said subject.

8. The system as recited in claim 1 wherein for one said visual display pair, said first display pattern includes a first circle and a reference mark adjacent thereto, and said second display pattern includes a second circle and a reference scale adjacent thereto, for simultaneous viewing of said pair by said subject for the measurement of cylophoria in said subject.

9. The system as recited in claim 1 wherein for one said visual display pair, said first display pattern includes a first pattern of diagonal lines and said second display pattern includes a second pattern of diagonal lines oriented oppositely to said first pattern of diagonal lines, for simultaneous viewing of said pair by said subject for the determination of eye dominance in said subject.

10. The system as recited in claim 1 wherein for one said visual display pair, said first display pattern comprises an illuminated dot and said second display pattern comprises an illuminated rectangular grid pattern, for simultaneous viewing of said pair by said subject in the testing for the presence of lateral and vertical phorias in said subject.

11. A vision testing system for measuring a plurality of vision function parameters of a subject, including, critical fusion frequency, stereopsis, visual activity, visual resolution, cyclophoria, eye dominance, and lateral and vertical phorias, which comprises:

a. first and second illuminated visual displays disposed for viewing along respective parallel first and second optical axes, each of said first and second displays comprising an array of a plurality of visual display patterns, one pattern of said first display and a corresponding pattern of said second display comprising a pair for simultaneous viewing by said subject, said first and second displays including a pair having dissimilar patterns, each pair being utilized in a particular vision test in the measurement of a corresponding vision function parameter;

b. said first display disposed for viewing by a first eye only of said subject along said first axis, and said second display disposed for viewing by the second eye only of said subject along said second axis;

c. said visual display patterns of each said first and second displays including an illuminated disk for use in measurement of critical fusion frequency, a rectangular array of four-dot sets for measurement of stereopsis, an array of Snellen E design as of various sizes and orientations for the measurement of visual acuity, and a resolution fan comprising a pattern of a plurality of radially extending alternate bright and dark contrast areas for the measurement of minimum visual resolution;

d. means for selectively illuminating said disk at a controllable frequency, and means for selectively varying said frequency, for the measurement of critical fusion frequency;

e. said first and second displays including a first pair including a pattern on said first display defining a first circle and reference mark adjacent thereto and a pattern on said second display defining a second circle and a reference scale adjacent thereto for the measurement of cyclophoria, a second pair including a pattern on said first display defining first diagonal lines and a pattern on said second display defining second diagonal lines oriented oppositely to said first diagonal lines for the determination of eye dominance, and a third pair including a pattern on said first display defining an illuminated dot and a pattern on said second display defining an illuminated rectangular grid pattern, for the testing for the presence of lateral and vertical phorias;

f. means for selectively controlling the illumination of said display patterns of each pair for viewing by said subject of any preselected pair in the measurement of the corresponding vision function parameter; and g. optical means including first and second eyepiece lenses disposed, respectively, along said first and second optical axes through which said first and second displays are viewed by respective first and second eyes of said subject, said eyepiece lenses configured to project images of each of said first and second displays to optical infinity.

12. The system as recited in claim 11 wherein said visual display patterns comprise light emitting diodes.

13. The system as recited in claim 11 further comprising recording means operable by said subject for verbally recording the identification of the selected vision parameter mesurement and the results of observations with respect to the said selected measurement.

14. A vision testing method for measuring a plurality of vision function parameters of a subject, comprising the steps of:

a. providing first and second illuminated visual displays disposed for viewing along respective parallel first and second optical axes, each of said first and second displays comprising an array of a plurality of visual display patterns, one pattern of said first display and a corresponding pattern of said second display comprising a pair for simultaneous viewing by said subject, said first and second displays including a pair having dissimilar patterns, each pair being utilized in a particular vision test in the measurement of a corresponding vision function parameter;

b. presenting said first display for viewing by a first eye only of said subject along said first axis, and presenting said second display for viewing by the second eye only of said subject along said second axis;

c. selectively controlling the illumination of said display patterns in pairs for viewing by said subject of any preselected pair for the corresponding vision function parameter measurement; and d. recording the identification of the selected vision function parameter measurement and the results of observations by said subject with respect to said selected measurement.

15. The method as recited in claim 14 wherein said visual display patterns comprise light emitting diodes.

16. The method as recited in claim 14 wherein said visual display patterns include an illuminated disk, and said method further comprises the steps of selectively illuminating said disk at a controllable frequency, and selectively varying said frequency, for the measurement of critical fusion frequency in the eyes of said subject.

17. The method as recited in claim 14 wherein said visual display patterns include a rectangular array of patterns comprising four-dot sets for the measurement of stereopsis in said subject.

18. The method as recited in claim 14 wherein said visual display patterns include an array of Snellen E designs of various sizes and orientations for the measurement of visual acuity of said subject.

19. The method as recited in claim 14 wherein said visual display patterns include a resolution fan comprising a pattern of a plurality of radially extending alternate bright and dark luminance areas for the measurement of minimum visual resolution of said subject.

20. The method as recited in claim 14 wherein for one said visual display pair, said first display pattern includes a first circle and a reference mark adjacent thereto, and said second display pattern includes a second circle and a scale adjacent thereto, and further comprises the step of presenting said pair including said first and second circles for simultaneous viewing by said subject for the measurement of cyclophoria in said subject.

21. The method as recited in claim 14 wherein for one said visual display pair, said first display pattern includes a first pattern of diagonal lines, and said second display pattern includes a second pattern of diagonal lines oriented oppositely to said first pattern of diagonal lines, and further comprises the step of presenting said pair including said first and second patterns of diagonal lines for simultaneous viewing by said subject for the determination of eye dominance in said subject.

22. The method as recited in claim 14 wherein for one said visual display pair, said first display pattern comprises an illuminated dot, and said second display pattern comprises an illuminated rectangular grid pattern, and further comprises the step of presenting said pair including said dot and grid for simultaneous viewing of said pair by said subject in the testing for the presence of lateral and vertical phorias in said subject.

* * * * *